US008535246B2

(12) United States Patent
Drennan et al.

(10) Patent No.: US 8,535,246 B2
(45) Date of Patent: Sep. 17, 2013

(54) SYSTEM AND METHOD OF REDUCING RISK AND/OR SEVERITY OF PRESSURE ULCERS

(75) Inventors: Denis Burke Drennan, Evanston, IL (US); Daniel William Southard, Folsom, CA (US)

(73) Assignee: DM Systems, Inc., Evanston, IL (US)

( * ) Notice: Subject to any disclaimer, the term of this patent is extended or adjusted under 35 U.S.C. 154(b) by 562 days.

(21) Appl. No.: 12/761,156

(22) Filed: Apr. 15, 2010

(65) Prior Publication Data

US 2010/0268122 A1 Oct. 21, 2010

Related U.S. Application Data

(60) Provisional application No. 61/169,804, filed on Apr. 16, 2009.

(51) Int. Cl.
*A61B 5/103* (2006.01)

(52) U.S. Cl.
USPC ......................................................... 600/587

(58) Field of Classification Search
USPC .......................................................... 600/587
See application file for complete search history.

(56) References Cited

U.S. PATENT DOCUMENTS

| 6,165,142 | A | * | 12/2000 | Bar ................................ 600/595 |
| 6,287,253 | B1 | * | 9/2001 | Ortega et al. .................. 600/300 |
| 6,646,556 | B1 | * | 11/2003 | Smith et al. ................. 340/573.1 |
| 2005/0131318 | A1 | | 6/2005 | Peifer et al. |
| 2005/0228317 | A1 | * | 10/2005 | Mathews ....................... 600/595 |
| 2008/0208063 | A1 | | 8/2008 | Brauers et al. |

* cited by examiner

*Primary Examiner* — Max Hindenburg
*Assistant Examiner* — Renee Danega
(74) *Attorney, Agent, or Firm* — Hartman Global IP Law; Gary M. Hartman; Domenica N. S. Hartman

(57) ABSTRACT

A pressure monitoring method and system for warning a patient or caregiver that soft tissue pressure has exceeded some predetermined level that over time would necessitate moving the patient to minimize or prevent soft tissue damage. The method and system entail the use of a pressure-sensitive pad assembly adapted to be applied to a surface of the patient's body and generate electrical outputs corresponding to soft tissue pressure sensed at the surface. The system monitors the electrical outputs over a preselected time period and generates a cumulative output signal based on the electrical outputs and corresponding to whether or not the soft tissue pressure has exceeded a predetermined pressure level during the preselected time period. The system generates audible and visual warnings if the cumulative output signal exceeds a predetermined cumulative threshold until the soft tissue pressure drops below the predetermined pressure level.

27 Claims, 2 Drawing Sheets

SYSTEM AND METHOD OF REDUCING RISK AND/OR SEVERITY OF PRESSURE ULCERS

CROSS REFERENCE TO RELATED APPLICATIONS

This application claims the benefit of U.S. Provisional Application No. 61/169,804, filed Apr. 16, 2009, and is related to U.S. patent application Ser. No. 10/950,128, filed Sep. 24, 2004. The contents of these prior applications are incorporated herein by reference.

BACKGROUND OF THE INVENTION

Pressure (decubitus) ulcers, commonly known as bedsores, present a serious problem to bedridden and wheelchair-confined patients. Prolonged pressure from a patient's body weight upon bony prominences is the most common cause of pressure ulcers. Prevention of and care for a preexisting pressure ulcer typically include treatment plans that involve relieving pressure on the exposed area by positioning and maintaining the patient off susceptible areas and any preexisting pressure ulcers, and minimizing localized pressure through the use of gel pads and similar types of products capable of absorbing and/or distributing pressure. However, such approaches can be insufficient if caregivers are unaware that a patient has shifted his/her weight onto prominences that are prone to pressure ulcers.

There are a wide variety of pressure sensors in the industrial and medical markets, some of which have found use in monitoring pressure ulcers. Notable examples include those that use air and fluid displacement techniques, as well as electromechanical analog devices. Many of these sensors are very portable and can be used to measure pressures at various locations of a patient at any point in time. There are also sheets of pressure sensors used primarily for research that give color-coded results from computer programs. The latter sensor type has been particularly used by manufacturers and some healthcare facilities to identify maximum tissue pressures under bed and wheelchair patients' skin areas. There are also a number of pressure monitoring devices, for example, the Oxford Pressure Monitor MKII with 12 Sensor system available from the Talley Group, Ltd., and the Pressure Alert system available from Cleveland Medical Devices, Inc.

It is believed that existing pressure monitoring systems do not provide a warning to a patient or caregiver relating to the actual risk of soft tissue damage to the patient based on the soft tissue pressure level and the duration that pressure has been applied.

BRIEF DESCRIPTION OF THE INVENTION

The present invention provides a pressure monitoring method and system suitable for providing a warning to a patient or caregiver that soft tissue pressure has exceeded some predetermined level that, over a sufficient period of time, would necessitate that the patient should move or be moved to prevent or at least minimize soft tissue damage.

According to a first aspect of the invention, the pressure monitoring system includes a pressure-sensitive pad assembly adapted to be applied to a surface of the patient's body that is susceptible to damage from soft tissue pressure. The pressure-sensitive pad assembly is adapted to generate electrical outputs corresponding to soft tissue pressure sensed by the pressure-sensitive pad assembly at the surface of the patient's body. The system further includes means for monitoring a plurality of the electrical outputs generated by the pressure-sensitive pad assembly over a preselected time period, and means for generating a cumulative output signal based on the plurality of the electrical outputs over the preselected time period and corresponding to whether the soft tissue pressure has exceeded a predetermined pressure level during the preselected time period and whether the soft tissue pressure dropped below the predetermined pressure level during the preselected time period. The system also has means for continuously generating a warning if the cumulative output signal exceeds a predetermined cumulative threshold until the soft tissue pressure sensed by the pressure-sensitive pad assembly drops below the predetermined pressure level.

According to a second aspect of the invention, a pressure monitoring method is provided that can be performed with the system described above. A particular aspect of the invention is for such a method to entail applying a pressure-sensitive pad assembly to a surface of the patient's body that is susceptible to damage from soft tissue pressure, monitoring a plurality of electrical outputs generated by the pressure-sensitive pad assembly over a preselected time period and corresponding to soft tissue pressure sensed by the pressure-sensitive pad assembly at the surface of the patient's body, generating a cumulative output signal based on the plurality of the electrical outputs over the preselected time period and corresponding to whether the soft tissue pressure has exceeded a predetermined pressure level during the preselected time period and whether the soft tissue pressure dropped below the predetermined pressure level during the preselected time period, and then continuously generating a warning if the cumulative output signal exceeds a predetermined cumulative threshold until the soft tissue pressure sensed by the pressure-sensitive pad assembly drops below the predetermined pressure level.

In view of the above, it can be seen that a significant advantage of this invention is that the pressure monitoring system of this invention is adapted to provide a warning to a patient or caregiver that specifically takes into consideration the actual risk of soft tissue damage to the patient based on the soft tissue pressure level, the duration the pressure has been applied, and any interruptions of the applied pressure. In particular, the system is adapted to warn the patient or caregiver if a sensed soft tissue pressure level exceeds a predetermined level and whose cumulative effect would necessitate that the patient should move or be moved to prevent further soft tissue damage. Currently, about 30 mmHg (about 4000 Pa) is believed to be universally accepted as a critical threshold pressure in the development of pressure ulcers. As such, the pressure monitoring system of this invention is preferably calibrated for maximum sensitivity at or near 30 mmHg. Another significant aspect of the invention is the ability to monitor pressure, generate a signal or alarm (e.g., audible and/or visual) in the event that pressure exceeds a pressure threshold for a predetermined period of time, and continue such a signal or alarm until the cause of the excessive pressure event has been appropriately addressed by the patient or a caregiver.

Other aspects and advantages of this invention will be better appreciated from the following detailed description.

DETAILED DESCRIPTION OF THE INVENTION

Figure 1:
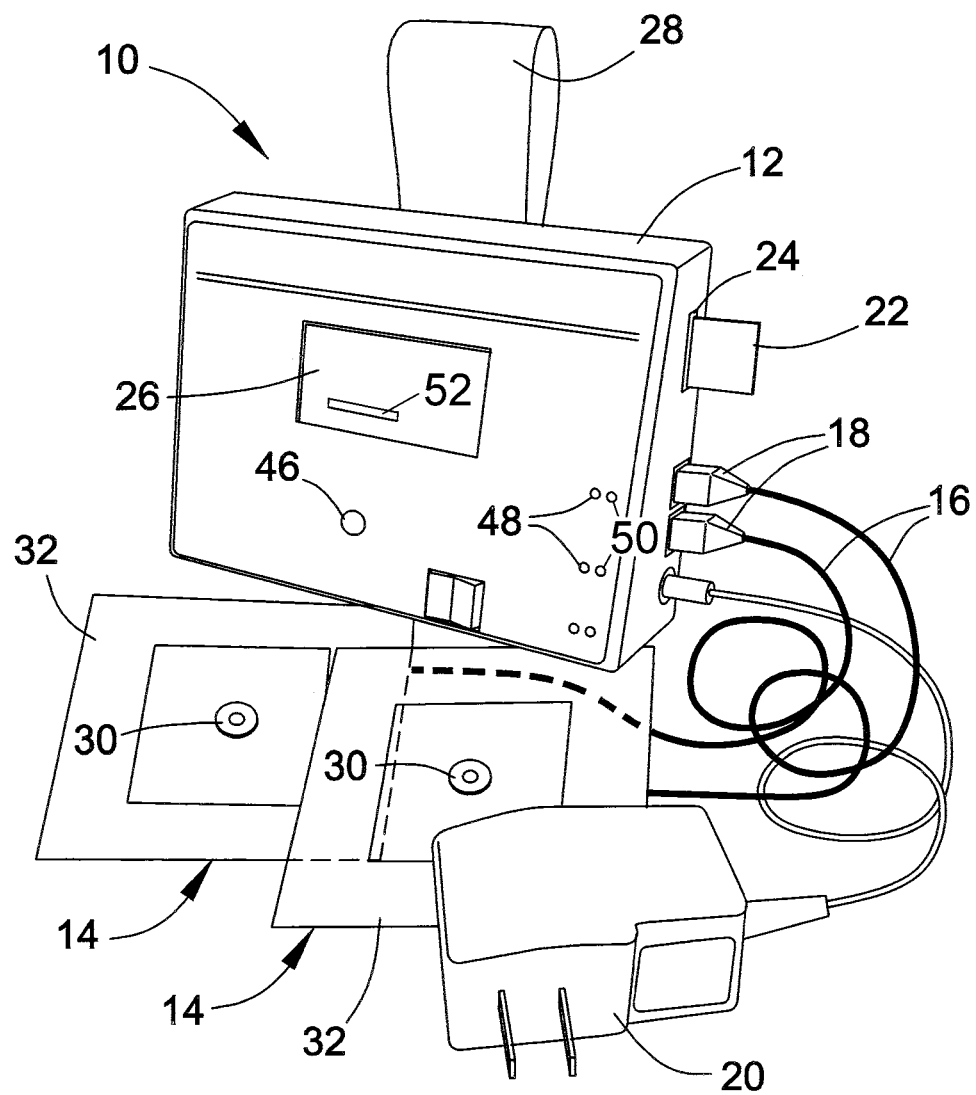
FIG. 1 represents components of a pressure monitoring system in accordance with an embodiment of this invention.

The present invention provides a pressure monitoring system whose primary function is to monitor a patient that is reclined or otherwise in a position that results in the patient's weight applying pressure to an area of the patient's body that is susceptible to pressure ulcers, such as soft tissue overlying a bony prominence. The pressure monitoring system further operates to correlate soft tissue pressure levels with time to warn if an applied pressure has met certain pressure and time thresholds that, in combination, are most likely to result in or exacerbate a pressure ulcer. Because a soft tissue pressure of 30 mmHg (about 4000 Pa) has become universally accepted as a critical threshold pressure in the development of pressure ulcers, a particularly suitable target value for the threshold pressure used by the system is about 30 mmHg, though more broadly a threshold pressure within a range of about 30 and about 34 mmHg (about 4000 to about 4500 Pa) are believed to be practical and acceptable. A variety of time periods may be utilized as suitable time thresholds (for example, ten, thirty, or sixty minutes) that can be selected by a caregiver. The selected time threshold serves as a time period during which the number and duration of pressure excursions above the threshold pressure are used to perform an assessment. If warranted, the assessment concludes with an alarm (e.g., audible and/or visual) that alerts caregivers and, if possible, the patient so that the patient can be repositioned in a timely manner to avoid or at least minimize the risk of a pressure ulcer. The type and level of the alarm can be selected to induce a conscious patient to move themselves in order to relieve the soft tissue pressure and stop the alarm, saving both tissue damage and the valuable time of a caregiver. As such, the monitoring system can also be viewed as a training device for patients who are cognitively aware and capable of repositioning themselves without assistance.

A significant feature of the invention outlined above is believed to be the correlation of pressure and time, combined with an alarm that is responsive to this correlation in order to reduce the likelihood that a patient will remain on fragile tissue or a pre-existing ulcer longer than is deemed to be clinically allowable. A preferred feature of the system is the ability to accurately detect soft tissue pressure above the threshold pressure, monitor the duration over which the pressure is above this threshold, and then either sound the alarm if the pressure remains above the threshold for the preselected time period or reset the time period if the soft tissue pressure is adequately relieved before the preselected time period is exceeded. In particularly preferred embodiments, the system utilizes a counter that is initiated to generate a cumulative output whose initial value is zero (e.g., time units such as seconds or minutes), begins to increase once the pressure threshold is exceeded, but gradually decreases back toward zero time units if the soft tissue pressure drops below the threshold. For example, the decrease in the counter value can occur at a predetermined ratio less than 1:1 relative to actual elapsed time, for example, at a ratio of one counter minute for every four actual minutes that have elapsed after the soft tissue pressure has dropped below the threshold. In this manner, the system operates to avoid soft tissue damage be taking into consideration not only how long the soft tissue pressure persisted above the pressure threshold, but also the elapsed time following a corrective measure taken prior to the end of the preselected time period if the corrective measure results in the soft tissue pressure dropping below the pressure threshold. Notably, the counter immediately resumes and its value again increases in actual time (1:1 ratio) if the patient moves to a position that resumes the excessive soft tissue pressure condition. Suitable electrical circuitry and timers for performing the counter function are commercially available and well within the capabilities of those skilled in the art, and therefore will not be discussed in any detail here.

In view of the above, it can be appreciated that optimal performance of the monitoring system will be achieved if the preselected time period is based on pressure ulcer risk assessments made by appropriately trained medical personnel. The monitoring system may also be equipped to retain clinical information regarding recent soft tissue pressure levels and durations, which can be useful to more fully assess a patient's history relating to the risk of soft tissue damage. Such historical data, which may further include patient clinical information and alarm events, can be retained by the system, such as with a memory card of a type commonly used in consumer electronics. This information can then be downloaded to a personal computer, printed and made a part of a patient's medical record, as well as downloaded onto electronic media for inclusion in a patient's hard or electronic medical record.

FIG. 1 is a schematic representation of one embodiment of the pressure monitoring system 10 of the present invention. The system 10 is shown as including a controller 12 and two pressure-sensitive pad assemblies 14 adapted to monitor soft tissue pressure at one or more surface regions of a patient's body that are susceptible to damage from soft tissue pressure. At least two pressure-sensitive pad assemblies 14 are preferably provided to allow multiple areas of concern to be simultaneously monitored, though it is foreseeable that a single pad assembly 14 may be sufficient under some circumstances. As evident from FIG. 1, the pad assemblies 14 are connected to the controller 12 through cables 16, preferably with connectors 18 configured to include a locking feature that prevents the pad assemblies 14 from becoming unintentionally disconnected from the controller 12. Though a "hard-wired" connection is shown, it should be understood that wireless connections are possible and could be used. The system 10 is further shown as including a power converter 20 of any suitable type capable of delivering an appropriate power level for electronics within the controller 12. The system 10 is also preferably capable of operating from battery power, such as for mobile uses (e.g., wheelchair) or in the event of a power outage. For this purpose, the controller 12 may contain a backup battery (not shown) or may be adapted to run off a battery of a self-propelled wheelchair.

A touchscreen 26 is provided by which the status of the system 10 can be conveyed to an operator, and with which the operator can configure the operation of the controller 12, including the selection of the time period as discussed above. The touchscreen 26 is preferably configured as a graphic user interface (GUI) that guides the user from screen to screen during setup of the system, such as when entering patient information and setting warning levels and thresholds, as well as for the purpose of controlling the download or transfer of information to or from the controller 12. Alternatively, a number/code pad could be used in place of the touchscreen 26. The touchscreen 26 preferably displays the preselected time period and whether the pressure being sensed by one of the pad assemblies 14 exceeds the pressure threshold (and optionally the actual pressure being sensed). According to a particularly preferred aspect of the invention, the controller 12 is also adapted to display an elapse time progress bar 52 on the touchscreen 26, which displays the total accumulated elapsed time that any one or more of the pad assemblies 14 has sensed a pressure exceeding the pressure threshold. The elapse time progress bar 52 displayed on the touchscreen 26 also preferably ramps backward at the same rate as the counter, providing a visual signal that alerts a caregiver as to any accumulating time condition that may exacerbate the pressure ulcer.

The controller 12 is also shown as equipped with a memory card 22 inserted in a memory card slot 24, which can be used to retain historical data relating to a patient as discussed previously. The controller 12 is also shown to further include a strap 28 that permits the controller 12 to be appropriately secured to a bed, wheelchair or other supportive structure near the patient.

Each pressure-sensitive pad assembly 14 is shown as having a pressure-sensitive device 30 centrally located within its generally square-shaped border 32. It should be noted here that alternative shaped pads may be used and preferred, for example, to cover curved body structures such as the heel. The pressure-sensitive devices 30 are adapted to generate electrical outputs corresponding to pressure, and particularly to soft tissue pressure to which the pad assemblies 14 are subjected when placed on a patient's body. In order for the system 10 to provide a reliable risk assessment, a feature of the invention is the type of pressure-sensitive device 30 used and its accuracy at the relatively low pressures of interest. While early prototypes of the present invention have made use of variable output pressure sensors, including Flex-Force® load sensors available from Tekscan, Inc., in later investigations pressure-sensitive contacts were determined to be well suited for use in the pressure monitoring system 10 of this invention. As such, for each occurrence in which the pressure sensed by one of the pressure-sensitive devices 30 exceeds the pressure threshold, the device 30 will generate an identical output level regardless of what extent the soft tissue pressure may exceed the pressure threshold.

Figure 2:
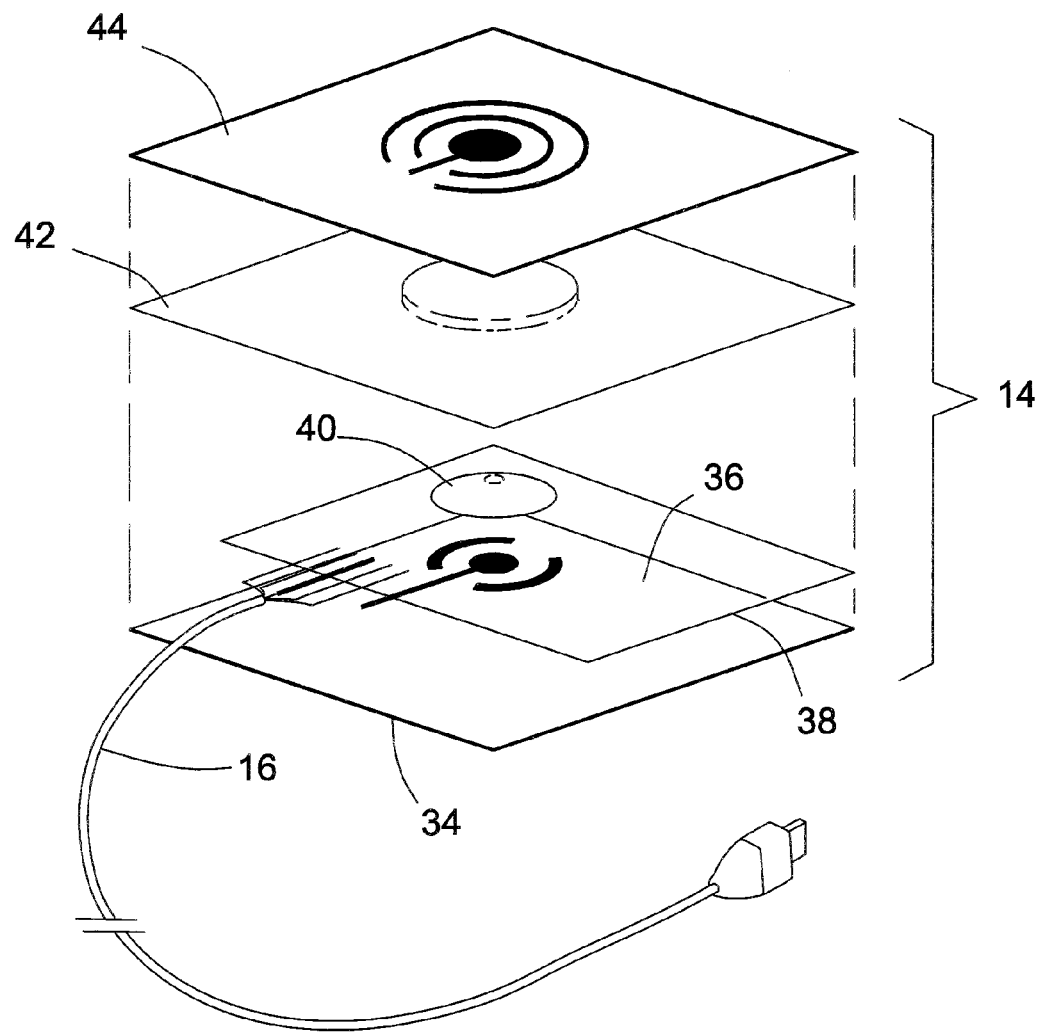
FIG. 2 represents an exploded view of a pressure sensing assembly of FIG. 1.

The construction of the pad assemblies 14 preferably allows each pad assembly 14 to be applied and secured to a patient's body, such as to one or more bony prominences that are most susceptible to damage from soft tissue pressure. As best seen in FIG. 2, each pad assembly 14 may have a multi-layer construction that includes a flexible circuit 34 on which conductive traces 36 have been formed, a support film 38 to which a conductive contact dome 40 is secured, a protective film 42 that lies on top of the film 38, and a soft fabric layer 44 that lies over the protective film 42. The pad assemblies 14 may further comprise additional or alternative layers, such as a disposable sleeve that can be slipped over or used in place the fabric layer 44 to allow reuse of the pad assembly 14. The conductive traces 36 are represented as defining a partial oval surrounding a contact. If the dome 40 is subjected to a sufficient force roughly normal to the flexible circuit 34, the dome 40 collapses and makes contact with the contact and completes (shorts) an electrical circuit containing the traces 36. The cable 16 is connected to the flexible circuit 34, such that electrical output signals generated by the completed electrical circuit can be transmitted to the controller 12. While the pad assembly 14 is represented as comprising a single dome 40, it is within the scope of the invention for any one or more of the pad assemblies 14 to comprise multiple domes 40, which may promote the reliability and accuracy of the system 10. As nonlimiting examples, two or more domes 40 may be used to define a linear pattern, three or more domes 40 may be used to define a triangular pattern, or four or more domes 40 may be used to define a rectilinear pattern.

In view of the foregoing, it should be apparent that the construction of the dome 40 largely determines the sensitivity and pressure threshold of the pressure-sensitive pad assemblies 14. Though various configurations are possible, in practice suitable results have been obtained with the RK series of domes commercially available from Snaptron, Inc. A particularly suitable dome is believed to be part number RK50040, which is reported to have a maximum trip force (Fmax) of about 40 grams. In investigations leading to this invention, a 40 gram trip force applied to the RK50040 dome has been correlated to a minimum pressure level of about 32.5 mmHg (about 4330 Pa). The RK50040 dome is available on a pressure-sensitive adhesive tape, which can serve as the support film 38 depicted in FIG. 2.

The controller 12 preferably contains circuitry (not shown) capable of monitoring electrical outputs generated by each pressure-sensitive pad assembly 14 over whatever time period has been selected by a caregiver. The controller 12 also preferably contains circuitry (not shown) adapted to generate the cumulative output signal (history alarm LED 50 and elapse time progress bar 52) of the counter based on the electrical outputs of each individual pad assembly 14 over the preselected time period. As previously described, the output value of the counter is cumulative in that it takes into consideration whether the soft tissue pressure has exceeded the preselected pressure level established by the pressure-sensitive device 30 during the preselected time period, as well as whether the soft tissue pressure dropped below the predetermined pressure level during the time period.

The controller 12 is further depicted in FIG. 1 as equipped with a speaker 46 and LEDs 48 adapted to generate, respectively, audible and visual warnings if the cumulative output signal (history alarm LED 50 and elapse time progress bar 52) of the counter exceeds a predetermined cumulative threshold. Each LED 48 is preferably individually associated with one of the pad assemblies 14. The warnings generated by the speaker 46 and LEDs 48 preferably continue until the soft tissue pressure sensed by the pressure-sensitive pad assembly 14 drops below the predetermined pressure level. A history alarm LED 50 is also shown as being associated with each of the pad assemblies 14, and is used as an indication of the accumulated alarm time on the counter. In a currently preferred embodiment of the invention, when the pressure sensed by a pad assembly 14 drops below the pressure threshold as a result of the patient being moved off the monitored pressure ulcer, both the audible alarm of the speaker 46 and the LED 48 associated with that pad assembly 14 turn off. However, the history alarm LED 50 preferably remains lit to indicate that time monitoring is continuing, i.e., the counter is above zero though decreasing in value as long as the patient remains off the pressure ulcer. As such, the history alarm LED 50 is able to draw a caregiver's attention to the elapse time progress bar 52, which will also be displayed on the touchscreen 26 while the history alarm LED 50 remains lit.

While the invention has been described in terms of a specific embodiment, it is apparent that other forms could be adopted by one skilled in the art. For example, the pressure monitoring system 10 and its components could differ in appearance and construction from the embodiment shown in FIGS. 1 and 2, the functions of each component could be performed by components of different construction but capable of a similar (though not necessarily equivalent) function, and various materials and assembly, calibration and test procedures could be used in the manufacturing and setup of the system 10. Other options include the use of different packaging, timer and pressure measurement modalities (including variable output pressure sensors), and the use of any number of pressure-sensitive pad assemblies 14 and devices 30, including different types of sensor technologies to measure a range of specific pressures. In addition, the predetermined pressure level could differ from 30 mmHg, though this pressure level is currently universally accepted as a critical threshold pressure in the development of pressure ulcers. The system can also be configured for use by home patients and wheelchair patients, as well as for placement in the shoes of ambulatory patients to measure and warn against excess foot pressure-time. The system can also be adapted for use in treating pre-existing wounds and to incorporate wound care dressings into the pressure-sensitive pad assembly, for example, by impregnating the pad assembly with topical antibiotics to aid in the treatment of bacterial infected wounds. Therefore, the scope of the invention is to be limited only by the following claims.

The invention claimed is:

1. A pressure monitoring system for providing a warning to a patient or caregiver that the patient should be moved to at least minimize soft tissue damage to the patient, the system comprising:
a pressure-sensitive pad assembly adapted to be applied to a surface of the patient's body that is susceptible to damage from soft tissue pressure, the pressure-sensitive pad assembly generating electrical outputs corresponding to soft tissue pressure sensed by the pressure-sensitive pad assembly at the surface of the patient's body;
means for monitoring a plurality of the electrical outputs generated by the pressure-sensitive pad assembly;
a counter associated with the monitoring means that generates a counter value that increases from an initial value while the soft tissue pressure exceeds a predetermined pressure level and decreases toward the initial value while the soft tissue pressure does not exceed the predetermined pressure level, wherein the counter value increases at a first ratio relative to actual elapsed time and the counter value decreases at a second ratio relative to actual elapsed time, and the second ratio is less than the first ratio; and
means for continuously generating a visual warning while the counter value exceeds the initial value.

2. The pressure monitoring system according to claim 1, wherein the visual warning comprises light and the generating means continuously emits the light if the counter value is above the initial value.

3. The pressure monitoring system according to claim 1, wherein the visual warning comprises an elapsed time progress bar that displays a total accumulated elapsed time that the soft tissue pressure sensed by the pressure-sensitive pad assembly exceeds the predetermined pressure level, and the elapsed time progress bar decreases at a rate corresponding to the second ratio of the counter while the soft tissue pressure does not exceed the predetermined pressure level.

4. The pressure monitoring system according to claim 1, wherein the pressure-sensitive pad assembly is adapted to generate the electrical outputs only if the soft tissue pressure exceeds the predetermined pressure level.

5. The pressure monitoring system according to claim 4, wherein the pressure-sensitive pad assembly generates the electrical outputs at an identical output level regardless of how much the soft tissue pressure exceeds the predetermined pressure level.

6. The pressure monitoring system according to claim 4, wherein the predetermined pressure level is within a range of about 4000 to about 4500 Pa.

7. The pressure monitoring system according to claim 4, wherein the predetermined pressure level is about 4000 Pa.

8. The pressure monitoring system according to claim 1, wherein the pressure-sensitive pad assembly comprises an electrically-conductive dome and conductive traces that are electrically shorted by the dome if the predetermined pressure level is exceeded.

9. The pressure monitoring system according to claim 8, wherein the dome is adapted to collapse and electrically short the conductive traces if subjected to a collapsing force of at least forty grams.

10. The pressure monitoring system according to claim 1, wherein the pressure-sensitive pad assembly is physically coupled to the monitoring means with an electrical connector and means for locking the electrical connector to the monitoring means.

11. The pressure monitoring system according to claim 1, further comprising means for generating an audible warning if the counter value is above the initial value and continuing to generate the audible warning until the soft tissue pressure sensed by the pressure-sensitive pad assembly drops below the predetermined pressure level.

12. A pressure monitoring method using the pressure monitoring system according to claim 1 to warn the patient or the caregiver that the patient should be moved to at least minimize soft tissue damage to the patient, the method comprising:
monitoring the plurality of the electrical outputs generated by the pressure-sensitive pad assembly over a preselected time period;
continuously generating the visual warning while the counter value exceeds the initial value; and
not generating the visual warning if the counter value does not exceed the initial value.

13. The pressure monitoring system according to claim 1, wherein the first ratio is about 1:1 relative to actual elapsed time.

14. The pressure monitoring system according to claim 1, wherein the second ratio is less than 1:1 relative to actual elapsed time.

15. The pressure monitoring system according to claim 1, further comprising a memory card on which are stored the soft tissue pressures and durations and alarm events of the monitoring system.

16. A method of monitoring pressure and providing a warning to a patient or caregiver that the patient should be moved to at least minimize soft tissue damage to the patient, the method comprising:
applying a pressure-sensitive pad assembly to a surface of the patient's body that is susceptible to damage from soft tissue pressure, the pressure-sensitive pad assembly generating electrical outputs corresponding to soft tissue pressure sensed by the pressure-sensitive pad assembly at the surface of the patient's body;
monitoring a plurality of the electrical outputs generated by the pressure-sensitive pad assembly;
generating a counter value that increases from an initial value while the soft tissue pressure exceeds a predetermined pressure level and decreases toward the initial value while the soft tissue pressure does not exceed the predetermined pressure level, wherein the counter value increases at a first ratio relative to actual elapsed time and the counter value decreases at a second ratio relative to actual elapsed time, and the second ratio is less than the first ratio; and
continuously generating a visual warning while the counter value exceeds the initial value.

17. The method according to claim 16, wherein the visual warning comprises light that is continuously emitted if the counter value is above the initial value.

18. The method according to claim 16, wherein the second ratio is less than 1:1 relative to actual elapsed time.

19. The method according to claim 16, wherein the electrical outputs of the pressure-sensitive pad assembly are produced only if the soft tissue pressure exceeds the predetermined pressure level.

20. The method according to claim 19, wherein the electrical outputs of the pressure-sensitive pad assembly are at an identical output level regardless of how much the soft tissue pressure exceeds the predetermined pressure level.

21. The method according to claim 19, wherein the predetermined pressure level is within a range of about 4000 to about 4500 Pa.

22. The method according to claim 19, wherein the predetermined pressure level is about 4000 Pa.

23. The method according to claim 16, further comprising continuously generating an audible warning if the counter value exceeds the initial value to alert the patient to move in order to relieve the soft tissue pressure from the surface of the patient's body.

24. The method according to claim 16, further comprising continuously generating an audible warning if the counter value exceeds the initial value to alert the caregiver to move the patient in order to relieve the soft tissue pressure from the surface of the patient's body.

25. The method according to claim 16, wherein the first ratio is about 1:1 relative to actual elapsed time.

26. The method according to claim 16, wherein the visual warning comprises an elapsed time progress bar that displays a total accumulated elapsed time that the soft tissue pressure sensed by the pressure-sensitive pad assembly exceeds the predetermined pressure level, and the elapsed time progress bar decreases at a rate corresponding to the second ratio of the counter while the soft tissue pressure does not exceed the predetermined pressure level.

27. The method according to claim 16, further comprising storing the soft tissue pressures and durations and alarm events of the monitoring system on a memory card.

\* \* \* \* \*